United States Patent [19]
Burke et al.

[11] Patent Number: 6,100,039
[45] Date of Patent: Aug. 8, 2000

[54] PROCESS FOR REVERSE TRANSCRIPTASE ACTIVITY MEASUREMENT USING FLUORESCENCE POLARIZATION

[75] Inventors: Thomas J. Burke, Madison; Randall E. Bolger, Oregon; Francis J. Lenoch, Madison, all of Wis.

[73] Assignee: Panvera, Inc., Madison, Wis.

[21] Appl. No.: 09/239,355

[22] Filed: Jan. 28, 1999

Related U.S. Application Data

[60] Provisional application No. 60/073,000, Jan. 29, 1998.
[51] Int. Cl.$^7$ .......................... C12Q 1/68; C07K 14/005; C07H 21/04
[52] U.S. Cl. ............................ 435/6; 530/350; 530/358; 536/23.1; 536/24.3
[58] Field of Search ................................ 435/6, 7.4, 7.72, 435/91.1, 974; 536/23.1, 24.3; 436/172; 530/350, 358

[56] References Cited

FOREIGN PATENT DOCUMENTS

| | | |
|---|---|---|
| 90301135.1 | 8/1990 | European Pat. Off. . |
| WO 93/14221 | 7/1993 | WIPO . |

OTHER PUBLICATIONS

Murakami et al., Fluorescent–labeled . . . , Nucleic Acids Research 19, 4097–4102, Jun. 6, 1991.

Checovich, W.J. et al. Flourescence polarization . . . , Nature 375, 254–256, May 18, 1995.

Maniatis et al., "cDNA cloning . . . " Molecular Cloning:A lab. Manual 8.29–8.86, Jan. 8, 1993.

Assay for Monitoring Human Immunodeficiency Virus Infection in and Antiviral Trial. *Journal of Clinical Microbiology*. Sep. 1988; vol. 26, No. 9; 1890–1892.

Chang, A et al., "Development of an Improved Product Enhanced Reverse Transcriptase Assay." *Journal of Virological Methods*. 1997; 65; 45–54.

Crespi, C. et al., "Microtiter Plate Assays for Inhibition of Human, Drug–Metabolizing Cytochromes P450." *Analytical Biochemistry*. 1997; 248; 188–190.

DiMarco, M.P.et al., "On–line Deconjugation of Glucuronides Using an Immobilized Enzyme Reactor Based Upon B–Glucuronidase." *Journal of Chromatography B*. 1998; 715; 379–386.

Eddershaw, P. et al., "Advances in In Vitro Drug Metabolism Screening." *PSTT*.

Ekstrand, D.H. et al., "A Sensitive Assay for the Quantification of Reverse Transcriptase Activity Based on the Use of Carrier–Bound Template and Non–Radioactive–Production Detection, With Special Reference to Human–Immunodeficiency–Virus Isolation." *Biotechnol. Appl. Biochem*. 1996; 23; 95–105.

Ethell, B. et al., "A Universal Radiochemical High–Performance Liquid Chromatographic Assay for the Determination of UDP–Glucuronosyltransferase Activity." *Analytical Biochemistry*. 1998; 255; 142–147.

Gupta, P. et al., "Detection of Human Immunodeficiency Virus by Reverse Transcriptase Assay, Antigen Capture Assay, and Radioimmunoassay." *Journal of Clinical Microbiology*. Jun. 198; vol. 25, No. 6; 1122–1125.

Hawes, Edward., "1996 ASPET N–Glucuronidation of Xenobiotics Symposium." *Drug Metabolism and Disposition*. 1998; vol. 26, No. 9; 830–837.

Heidrun, M. et al., "Radioassay of UDP–Glucuronosyltranferase Activites Toward Endogenous Substrates Using Labeled UDP–Glucuronic Acid and an Organic Solvent Extraction Procedure." *Analytical Biochemistry*. 1994; 219; 182–188. Jan. 1999; vol. 2, No. 1; 13–19.

Jolley, M.E., "Flourescence Polarization Immunoassay for the Determination of Therapeutic Drug Levels In Human Plasma." *Journal of Analytical Toxicology*. Sep./Oct. 1981; 5; 236–240.

Lo, W. et al., "One–Step Fluorescent Probe Product–Enhanced Reverse Transcriptase Assay." *Biotechniques*. Jul. 1998; vol. 25, No. 1, 98–106.

Pritchard, M. et al., "A Method for the Determination of UDP–Glucuronosyltransferase Activity Toward Arylcarboxylic Acids.", *Analytical Biochemistry*, 1993; 212; 487–497.

Sano, K. et al., "Comparison of the Sensitivites of Two Non–Isotopic Reverse Transcriptase (RT) Assays for Human Immunodeficiency Virus Type 1 RT." *Journal of Virological Methods*. 1996; 58; 199–204.

Sperker,B. et al., "High–Performance Liquid Chromatographic Quantification of 4–Methylumbelliferyl–B–D–Glucuronide As a Probe for Human B–Glucuronidase Activity in Tissue Homogenates." *The Journal of Chromatography B*. 1996; 685; 181–184.

Taylor,P et a., "Kinetic and Mutational Anaylsis of Human Immunodeficiency Virus Type 1 Reverse Transcriptase Inhibition by Inophyllums, a Novel Class of Non–nucleoside Inhibitors. " *The Journal of Biological Chemistry*, Mar. 4, 1994; vol. 269, No. 9; 6325–6331.

Woo, L. et al., "Active Site Directed Inhibition of Estrone Sulfatase by Nonsteroidal Coumarin Sulfamats. " *J. Med. Chem*. 1996; 39, 1349–1351.

(List continued on next page.)

*Primary Examiner*—David Guzo
*Assistant Examiner*—Jon Shuman
*Attorney, Agent, or Firm*—Mark K. Johnson

[57] ABSTRACT

Described is a process for detecting reverse transcriptase activity and, thereby, reverse transcriptase inhibitors using fluorescence polarization, comprising, mixing a DNA primer with an RNA template. Then forming an RNA/DNA duplex utilizing the reverse transcriptase and removing the RNA from the RNA/DNA duplex to form single-stranded DNA. Finally, adding a fluorescent-labeled oligonucleotide complementary to the single-stranded DNA for hybridizing to the single-stranded DNA; and, measuring the fluorescence polarization.

19 Claims, 8 Drawing Sheets

OTHER PUBLICATIONS

Wosikowski, K. et al., "Identification of Epidermal Growth Factor Receptor and c–erbB2 Pathway Inhibitors by Correlation With Gene Expression Patterns." *Journal of the National Cancer Institute.* Oct. 15, 1997; vol. 89, No. 20; 1505–1515.

Yamamoto, S. et al., "Highly Sensitive Qualitative and Quantitative Detection of Reverse Transcriptase Activity: Optimization, Validation and Comparative Anaylsis With Other Detection Systems." *Journal of Virological Methods.* 1996; 61; 135–143.

Bansal, S. et al., :A Unified Method for the Assay of Uridine Diphosphoglucuronyltransferase Activities Toward Various Aglycones Using Uridine Diphospho (U–14C) Glucoronic Acid. *Analytical Biochemstry.* 1980; 321–329.

Bruisten, S. et al., "Detection of HIV–1 Distrubution in Different Blood Fractions by Two Nucleic Acid Amplification Assays." *Aids Research and Human Retroviruses.* 1993; vol. 9, No. 3; 259–265.

Burger, H. et al., "Comparison of Antigen Immunoassay and Reverse Transcriptase".

a. Annealing

Oligo dT primer (12-18 bases)    5' ─────── 3'
                                   | | | | | |
Poly rA template (300 bases)     3' ──────────────── 5'

↓ Polymerase Reaction (incubate at 37°C for 30 min.)

b. Double-stranded RNA/DNA Duplex

5' ──────────────────────────────────── 3'
   | | | | | | | | | | | | | | | | | | | | | | | | |
3' ──────────────────────────────────── 5'

↓ Add NaOH to hydrolyze RNA strand c. Single-stranded DNA

──────────────────────────────────────
| | | | | | | | | | | | | | | | | | | | | | | | |

─────O   Add Fluorescent-labeled Oligo dA

Low Polarization

↓ d. Fluorescent-labeled Oligo dA Hybridized to Complementary DNA Strand

──────────────────────────────────────
| | | | | | | | | | | | | | | | | | | | | | | | |
──O ──O ──O ──O

High Polarization

Read Time (minutes)
Read Time 16 Hours

Figure 8.

PROCESS FOR REVERSE TRANSCRIPTASE ACTIVITY MEASUREMENT USING FLUORESCENCE POLARIZATION

CROSS-REFERENCE TO RELATED APPLICATIONS

This application claims the priority of U.S. provisional application, 60/073,000, filed Jan. 29, 1998.

FEDERALLY SPONSORED RESEARCH

N/A

FIELD

The field of this invention relates to a process for the detection of reverse transcriptase (RT) activity using fluorescence polarization. More particularly the process is a homogeneous method that can be used to identify reverse transcriptase inhibitors.

BACKGROUND

A reverse transcriptase is an enzyme that catalyzes RNA dependent DNA synthesis and is an indispensable component of replication-competent retroviruses. Reverse transcriptases direct extension of the 3' end of a DNA strand one deoxynucleotide at a time and cannot initiate synthesis de novo but require a DNA or RNA primer. Typically, reverse transcriptases also possess two additional enzymatic activities: 1) DNA dependent DNA polymerase and 2) RNase H activity. There is a significant amount of research on retroviruses and their inhibitors because of their role in AIDS and other pathologies such as leukemia.

In AIDS research, there are several approaches for antiviral therapy and three classes of antiviral drugs are currently available: nucleoside reverse transcriptase inhibitors, non-nucleoside reverse transcriptase inhibitors, and protease inhibitors. Assays that can detect reverse transcriptase inhibitor activity are important in identifying new inhibitors for use in preventing disease.

Because reverse transcriptase enzymes are essential to replication-competent virions, specifically inhibiting their activity in one method of abating viral propagation. Many methods have been developed for detecting reverse transcriptases, their activity, and their products and the literature can be quite confusing on this. For clarification, a summary of some of the methods is compiled in the table below.

| Target | Assay Type |
| --- | --- |
| Detection of RT protein | Antigen capture assay and radioimmunoasssay |
| Detection of RT gene | PCR amplification of gene |
| Detection of RT protein | Immunoassay |
| Detection of RT enzymatic products | PCR and fluorescence detection |
| Detection of RT enzymatic products | Direct detection of products |
| Detection of RT enzymatic products | RT assay combined with PCR detection of product |
| Detection of RT enzymatic products | Microtiter immunoasssay detected modified nucleotides in RT enzymatic product |
| Detection of RT enzymatic products | Microtiter assay with immobilized template and primer |
| Detection of RT enzymatic products | ELISA and non-isotopic detection method |
| Detection of RT enzymatic products | Scintillation Proximity Assay (radioactive) |
| Detection of RT enzymatic products | RT assay of unique RNA template combined with PCR detection of product |

Gupta, P., Balachandran, R., Grovit, K., Webster, D., and Rinaldo C, J. (1987) Detection of human immunodeficiency virus by reverse transcriptase assay, antigen capture assay, and radioimmunoassay. *J Clin Microbiol* 25(6), 1122–5; Bruisten, S., van Gemen, B., Koppelman, M., Rasch, M., van Strijp, D., Schukkink, R., Beyer, R., Weigel, H., Lens, P., and Huisman, H. (1993) Detection of HIV-1 distribution in different blood fractions by two nucleic acid amplification assays. *AIDS Res Hum Retroviruses* 9(3), 259–65; Burger, H., Paul, D., Siegal, F. P., Wendel, I., Neff, S., Eilbott, D., Gehan, K., Grimson, R., and Weiser, B. (1988) Comparison of antigen immunoassay and reverse transcriptase assay for monitoring human immunodeficiency virus infection in an antiviral trial. *J Clin Microbiol* 26(9), 1890–2; Arnold, B. A., Hepler, R. W., and Keller, P. M. (1998) One-step fluorescent probe product-enhanced reverse transcriptase assay. *Biotechniques* 25(1), 98–106; Chang, A., Ostrove, J. M., and Bird, R. E. (1997) Development of an improved product enhanced reverse transcriptase assay. *J Virol Methods* 65(1), 45–54; Ekstrand, D. H., Awad, R. J., Kallander, C. F., and Gronowitz, J. S. (1996) A sensitive assay for the quantification of reverse transcriptase activity based on the use of carrier-bound template and non-radioactive-product detection, with special reference to human-immunodeficiency-virus isolation. *Biotechnol Appl Biochem* 23(Pt 2)), 95–105; Nakano, T., Sano, K., Odawara, F., Saitoh, Y., Otake, T., Nakamura, T., Hayashi, K., Misaki, H., and Nakai, M. (1994) An improved non-radioisotopic reverse transcriptase assay and its evaluation. *Kansenshogaku Zasshi* 68(7), 923–3 1; Sano, K., Odawara, F., and Nakai, M. (1996) Comparison of the sensitivities of two non-isotopic reverse transcriptase (RT) assays for human immunodeficiency virus type 1 RT. *J Virol Methods* 58(1–2), 199–204; Taylor, P. B., Culp, J. S., Debouck, C., Johnson, R. K., Patil, A. D., Woolf, D. J., Brooks, I., and Hertzberg, R. P. (1994) Kinetic and mutational analysis of human immunodeficiency virus type 1 reverse transcriptase inhibition by inophyllums, a novel class of non-nucleoside inhibitors. *J Biol Chem* 269(9), 6325–31; Yamamoto, S., Folks, T. M., and Heneine, W. (1996) Highly sensitive qualitative and quantitative detection of reverse transcriptase activity: optimization, validation, and comparative analysis with other detection systems. *J Virol Methods* 61(1–2), 135–43.

Many different types of assays exist for reverse transcriptases. Some of these assays detect the reverse transcriptase activity by detecting the enzymatic products either directly or after amplification of the signal. Other detection assays measure the physical amount of reverse transcriptase by using immunoassays of the enzyme or amplification of the gene encoding the reverse transcriptase.

SUMMARY

A process to measure reverse transcriptase activity is described in order to identify RT inhibitors. The process may not be as sensitive as assays which include a signal amplification step such as immunoassays or PCR assays but offers a distinct advantage of homogeneity: the process can be performed by sequential addition of reagents to a microtiter plate followed by direct measurement of the fluorescence polarization value.

Several inhibitors of reverse transcriptases have been identified and some have been used to treat retroviral diseases such as AIDS. Retroviruses have high mutation rates therefore the rate of acquired drug resistance can be a severe problem in treatment of disease. Therefore it is necessary to continuously find new drugs to treat mutated forms of the retrovirus. The process described detects reverse transcriptase inhibitor activity.

Disclosed is a process comprising a homogeneous in vitro assay to detect reverse transcriptase activity that provides a screen for new inhibitors in a high throughput format. Using a fluorescence polarization format, no immobilization of molecules, separation steps, or radioisotope are required. The assay can be performed in a single assay or can be performed in microtiter plates in high throughput screening applications.

In a preferred embodiment, a process is disclosed for detecting reverse transcriptase activity using fluorescence polarization, comprising, mixing a primer with an RNA template, then forming an RNA/DNA duplex utilizing the reverse transcriptase and removing the RNA from the RNA/DNA duplex thereby forming a single-stranded DNA. Finally, measuring the fluorescence polarization of a fluorescent-labeled oligonucleotide complementary to the single-stranded DNA; adding the oligonucleotide for hybridizing to the single-stranded DNA; and, comparing the fluorescence polarization before and after hybridization.

In a preferred embodiment, a process is disclosed for quantifying formation of DNA from RNA by a reverse transcriptase, comprising, adding an RNA template to a solution to determine the activity of a reverse transcriptase and presence of reverse transcriptase inhibitors, then forming an RNA/DNA duplex if the reverse transcriptase is present. Next, forming a single-stranded DNA by removing the RNA from the RNA/DNA duplex and adding a light emitting labeled oligonucleotide, having a known polarization value and complementary to the single-stranded DNA for hybridizing to the single-stranded DNA. Finally, measuring activity of the reverse transcriptase by comparing polarization values of the light emitting labeled oligonucleotide before and after hybridization. The process further comprising removing the RNA by adding an RNA removing enzyme, wherein the light emitting labeled oligonucleotide comprises a fluorescent-labeled oligonucleotide.

In a preferred embodiment, a mixture is disclosed for measuring reverse transcriptase activity, comprising, an RNA template; a plurality of DNA nucleotides complementary to the RNA template; an RNA removing enzyme for removing RNA from an RNA/DNA hybrid thereby forming single-stranded DNA, and a light emitting labeled oligonucleotide complementary to the single-stranded DNA.

The oligo-dT that is used to prime the reverse transcriptase reaction may not be hybridized to the poly-rA, however it can hybridize in the detection system to the fluorescein labeled oligo-dA. In a preferred embodiment, an RNA template may have a unique sequence at the 3' end that is used to prime the reverse transcriptase reaction. This serves two functions: it insures that the primer is at the end of the template and it keeps the primer from interfering with the detection method. Because the primer is at the end of the template, the activity would be higher because the length of the strand synthesized would be longer. A 15–25 base primer may be used for this purpose.

In a preferred embodiment, the fluorescent oligo may be labeled differently so that when in hybridizes, the shift in polarization is higher. For example, DTAF may be used to label the oligo. The length of this space or arm connecting the oligo to the fluorescent molecule may be adjusted so that when the oligo hybridizes, it has a larger shift in polarization.

In a preferred embodiment, the fluorescent oligo has multiple fluorescent molecules attached increasing the sensitivity of the assay.

In a preferred embodiment, fluorescent labels other than fluorescein may be used. The non-fluorescein labels:
are not as sensitive to pH,
are brighter, they absorbing and emitting light at different wavelengths,
have different ionic charges,
have different hydrophobic characteristics,
have different extinction coefficients,
have different Stokes shifts,
are more inert and therefore interact less with the container and molecules in the mixture,
allow a simpler coupling mechanism between the oligo and the fluorescent molecule, In a preferred embodiment, the size of the fluorescent oligo may be changed. A shorter oligo allows a higher shift in polarization when it hybridizes to the template. This also allows more fluorescent molecules to be incorporated.

In a preferred embodiment, a reaction mixture may be formed which contains all the components for the detection. This allows one to do the reverse transcriptase reaction for a specified period of time before adding a single mixture that hydrolyzes the RNA and yet allows the oligo to hybridize.

In a preferred embodiment, the process may be successful on templates other than the homopolymers described. It utilizes a unique RNA sequence but blocking oligos may be necessary in the hybridization step with the fluorescent oligo. A unique RNA sequence may have some secondary structure that allows intrastrand hybridization.

The sodium hydroxide in this assay inactivates the reverse transcriptase and kills both the enzymatic activity and the nucleic acid binding activity. In a preferred embodiment sodium hydroxide may be eliminated and enzymes used to remove the RNA template. Reagents may be included to inactivate the DNA binding activity of the reverse transcriptase.

In a preferred embodiment, the ionic strength of the hybridization reaction may be optimized to give a larger shift in polarization and to obtain rapid detection of hybridization. Magnesium chloride, EDTA, and other ionic salts improve the assay. There are many reagents known in the industry which facilitate better nucleic acid hybridization. These include polymers, detergents, chaeotropic agents, and their re-agents can protect the nucleic acid from binding to the container. Some of these agents may be added to the hybridization reaction to give better results.

Reference is now made in detail to the preferred embodiments of the invention, examples of which are illustrated in the accompanying drawings.

DETAILED DESCRIPTION

Definitions of Terms:

Nucleic Acids, Nucleic Acid Structures and Their Components

The term "nucleotide" refers to any ribonucleotide monophosphate and deoxyribonucleotide monophosphate with any natural or modified base in that structure that occurs in polymerized form as a component of a nucleic acid. The terms "rNTP" and "dNTP" refer to a ribonucleotide triphosphate respectively a deoxyribonucleotide triphosphate with any natural or modified base. The terms "rNTPs" and "dNTPs" refer to a mixture of ribonucleotide triphosphates respectively deoxyribonucleotide triphosphates consisting of at least two different ribonucleotide triphosphates or deoxyribonucleotid triphosphates.

The term "nucleic acid" refers to a single or partly or completely double-stranded oligomer or polymer. If the nucleic acid consists entirely of ribonucleotide monophosphates it is a "RNA", if it consists entirely of deoxyribonucleotide monophosphates, it is a "DNA". However, a nucleic acid may contain both ribonucleotide monophosphates and deoxyribonucleotide monophosphates. The terms "ss" and "ds" characterize a nucleic acid as single-stranded or double-stranded.

The term "oligonucleotide" refers to a single-stranded nucleic acid consisting of at least two, but not more than one hundred, natural or modified nucleotides or a mixture of these. The oligonucleotide can be or be derived from a natural nucleic acid, or it may be produced by chemical or enzymatic synthesis.

The term "polynucleotide" refers to a single-stranded or double-stranded nucleic acid consisting of more than one hundred natural or modified nucleotides or a mixture of these.

The term "homopolymer" describes nucleic acids or segments of nucleic acids whose nucleotides consist of a single base. This includes bases that are only identical to a complementary base with regard to their binding function, while their chemical structures are different.

The term "heteropolymer" describes nucleic acids or segments of nucleic acids whose nucleotides consist of at least two bases that are different with regard to their binding function to a complementary base.

The terms "upstream" and "downstream" indicate the relative location resp. direction within a nucleid acid strand. Looked upon from a reference element, "upstream" refers to a location or direction towards the 5'-end, "downstream" towards the 3'-end.

Enzymes and Enzymatic Activities

The term "reverse transcriptase" refers to an enzyme that in its natural function, in a primer-dependent reaction and by using dNTPs, synthesizes a DNA complementary to a template RNA.

The term "reverse transcriptase activity" refers to the activity of any enzyme by which in a primer-dependent reaction and by using dNTPs a DNA complementary to a template RNA is synthesized.

The term "RNA polymerase", or "DNA-dependent RNA polymerase" refers to an enzyme which in sequence-specific manner binds to a transcription promoter, initiates the transcription of an RNA starting from a defined position downstream of this transcription promoter, and which, from a single-stranded or double-stranded DNA and by using rNTPs, synthesizes an RNA complementary to the transcribed DNA strand.

The term "DNA polymerase" or "DNA-dependent DNA polymerase" refers to an enzyme which, in a primer-dependent reaction and by using dNTPs, synthesizes a DNA strand complementary to a DNA strand.

The term "RNA replicase" refers to an enzyme or complex of enzymes with RNA-dependent RNA polymerase activity capable of replicating, by using rNTPs, a replicative RNA matched to the RNA replicase, the result of the replication process being a new molecule of replicative RNA which is complementary to the replicated replicative RNA.

Functional Sequences and Functions

The term "functional sequence" refers to a segment on the strand of a nucleic acid that exerts a certain function in the assay. This function is exerted by the nucleic acid by which the functional sequence is introduced, and/or by a subsequent single-stranded nucleic acid derived thereof that has an identical or complementary base sequence, or by a double-stranded nucleic acid. The base sequence contained in a functional sequence is either precisely defined by its function or can be chosen freely.

The term "hybridization sequence" refers to a functional sequence that, for the purpose of hybridization to another nucleic acid, has a base sequence complementary to the hybridization sequence of the other nucleic acid.

The term "flanking sequence" refers to a functional sequence that forms the 5' or 3'-end of a nucleic acid either upstream or downstream of any other functional sequence.

The term "spacer sequence" refers to a functional sequence that serves the function of separating two other functional sequences on a nucleic acid from each other.

Nucleic Acids with Defined Function

The term "primer" refers to a nucleic acid of a sequence that is complementary to another nucleic acid. When hybridized to that nucleic acid the primer, by means of its free 3'-hydroxy group, serves as the point at which the synthesis of a nucleic acid strand by an RT activity or a DNA-dependent DNA polymerase is initiated.

The term "RT primer" refers to the primer that exerts the function of a primer for the RT activity.

The term "template nucleic acid" refers to the single-stranded nucleic acid to which, at least in part, a complementary DNA strand is synthesized by reverse transcriptase activity.

The term "template RNA" refers to those parts of a template nucleic acid that consist of RNA and to which, at least in part, a cDNA is synthesized.

The term "template DNA" refers to those parts of a template nucleic acid that consist of DNA.

The term "template-primer combination" refers to the combination of a template nucleic acid with all nucleic acids hybridized to it, including RT primers, that is used as substrate for the RT or RT activity.

The term "cDNA" refers to the nucleic acid that consists of the DNA complementary to the template nucleic acid that has been synthesized by the RT activity, as well as all components of the RT primer.

The term "cDNA/template duplex" refers to a at least in part double-stranded nucleic acid which consists of the template nucleic acid and the cDNA hybridized to it.

The term "cDNA/RNA heteroduplex" refers to those segments of a cDNA-template duplex that consist of the template RNA and the cDNA hybridized to it.

The term "retroelement" refers to genetic elements and their expression products that have been generated by reverse transcriptase activity and/or replicate themselves by means of reverse transcriptase.

The term "carrier" refers to a solid phase consisting, e.g., of beads, the surface of a well of a microtiter plate, or a filter membrane.

Fluorescence Polarization

Fluorescence polarization is a versatile laboratory technique for measuring equilibrium binding, nucleic acid hybridization, and enzymatic activity. Fluorescence polarization assays are homogeneous in that they do not require a separation step such as centrifugation, filtration, chromatography, precipitation or electrophoresis. These assays are done in real time, directly in solution and do not require an immobilized phase. Polarization values can be measured repeatedly and after the addition of reagents since measuring the polarization is rapid and does not destroy the sample. Generally, this technique can be used to measure polarization values of fluorophores from low picomolar to micromolar levels. This section describes how fluorescence polarization can be used in a simple and quantitative way to measure enzyme activity, particularly the activity of reverse transcriptase.

When a fluorescently labeled molecule is excited with plane polarized light, it emits light that has a degree of polarization that is inversely proportional to its molecular rotation. Large fluorescently labeled molecules remain relatively stationary during the excited state (4 nanoseconds in the case of fluorescein) and the polarization of the light remains relatively constant between excitation and emission. Small fluorescently labeled molecules rotate rapidly during the excited state and the polarization changes significantly between excitation and emission. Therefore, small molecules have low polarization values and large molecules have high polarization values. For example, a single-stranded fluorescein-labeled oligonucleotide has a relatively low polarization value but when it is hybridized to a complementary strand, it has a higher polarization value.

Fluorescence polarization (P) is defined as:

$$P = \frac{Int_\parallel - Int_\perp}{Int_\parallel + Int_\perp}$$

Where || is the intensity of the emission light parallel to the excitation light plane and Int⊥ is the intensity of the emission light perpendicular to the excitation light plane. P, being a ratio of light intensities, is a dimensionless number. The Beacon® and Beacon 2000™ System used in these experiments expresses polarization in millipolarization units (1 Polarization Unit =1000 mP Units).

The relationship between molecular rotation and size is described by the Perrin equation and the reader is referred to Jolley, M. E. (1991) in *Journal of Analytical Toxicology*, pp. 236–240, which gives a thorough explanation of this equation. Summarily, the Perrin equation states that polarization is directly proportional to the rotational relaxation time, the time that it takes a molecule to rotate through an angle of approximately 68.5 degrees. Rotational relaxation time is related to viscosity (η), absolute temperature (T), molecular volume (V), and the gas constant (R) by the following equation:

$$\text{Rotational Relaxation Time} = \frac{3\eta V}{RT}$$

The rotational relaxation time is small (≈1 nanosecond) for small molecules (e.g. fluorescein) and large (≈100 nanoseconds) for large molecules (e.g. immunoglobulins). If viscosity and temperature are held constant, rotational relaxation time, and therefore polarization, is directly related to the molecular volume. Changes in molecular volume may be due to interactions with other molecules, dissociation, polymerization, degradation, hybridization, or conformational changes of the fluorescently labeled molecule. For example, fluorescence polarization has been used to measure enzymatic cleavage of large fluorescein labeled polymers by proteases, DNases, and RNases. It also has been used to measure equilibrium binding for protein/protein interactions, antibody/antigen binding, and protein/DNA binding. Fluorescence polarization is a simple and economical way to measure reverse transcriptase activity and to screen for inhibitors.

Detection of Nucleic Acid Hybridization by Fluorescence Polarization

In this detection process, a light-emitting label is attached to an oligonucleotide (oligo). In a preferred embodiment the light-emitting labeled oligo comprises a fluorescently labeled oligonucleotide that has a low polarization value when single-stranded but increases upon hybridizing to a complementary strand. In a preferred embodiment, the tracer (fluorescent oligo) is a homopolymer dA (DNA homopolymer Adenosine), which allows it to hybridize anywhere along the dT (DNA homopolymer Thymidine) strand that was synthesized by the reverse transcriptase. This invention allows for a more sensitive signal since the entire dT template can be hybridized by a single oligo.

The process is based on the observation that reverse transcriptase can synthesize an RNA/DNA hybrid and that the amount of hybrid made is proportional to the amount of reverse transcriptase activity. The RNA can be removed by denaturation or more simply, by base hydrolysis, producing a single-stranded DNA. The amount of single-stranded DNA can then be quantitatively measured by hybridizing it to complementary fluorescently labeled oligonucleotides. The low polarization value of the oligonucleotide go up when it hybridizes to the larger DNA strand. The increase in polarization value of the oligonucleotide is directly proportional to the amount of complementary single-stranded DNA that is present. Using an RNA homopolymer adenine enhances the assay sensitivity, producing a homopolymer of thymidine, easily detected with fluorescent oligo-dA, which binds throughout the length of the longer DNA.

Reverse transcriptase activity can be measured without an inhibitor present. That measurement is then compared to reverse transcriptase activity when an inhibitor is present to determine the functionality of a specific inhibitor. An active reverse transcriptase inhibitor will hinder or prevent formation of RNA/DNA hybrid and, therefore, single-stranded DNA. Without the presence of single-stranded DNA, the labeled oligonucleotide has nowhere to hybridize and maintains its low polarization value, which indicates a functional inhibitor. A level of functionality can be measured by creating a scale with the polarization value of the labeled oligonucleotide alone on the low end and the polarization value of the labeled oligonucleotide after reverse transcription on an RNA template without an inhibitor present on the high end. A polarization measurement with an inhibitor present is then compared to the high and low values.

EXAMPLES

The Reverse Transcriptase Activity Detection assays were performed using a Beacon™ 2000 Analyzer. The following reagents were purchased from commercial sources: fluorescein-labeled oligo dA-F (Bio.Synthesis Corp., Lewisville, Tex.), AMV Reverse Transcriptase (Promega Corp., Madison, Wis.), and Polyadenylic Acid Poly A (Pharmacia Biotech, Milwaukee, Wis.). The assay requires a reverse trancriptase reaction step followed by a fluorescence polarization-based detection step. The reverse transcriptase reactions were completed using the directions accompanying the kit. In the reaction 20 ng of Oligo (dT) were annealed to 1 µg of Poly A at 70° C. for 5 minutes. The annealed reactions were added to an RT mix containing RT buffer and dTTP nucleotides with varying units of reverse transcriptase (30, 15, 7.5, 3.8, and 1.9 Units/Rxn). Reactions were incubated at 37° C. in a water bath. 5 µl aliquots were quenched at 5, 10, 15, 20, 25, 30, 45, and 60 minutes by adding the aliquots to a tube containing 20 µl of 125 mM NaOH. For the detection step, a 75 µl aliquot of oligo dA-F in 0.5 M Tris, pH 7.5, was added to each quenched reaction. The samples were incubated for 10 minutes at room temperature. Fluorescence polarization in each sample was measured using the Beacon™ 2000 Analyzer.

Example 1

Figure 1:
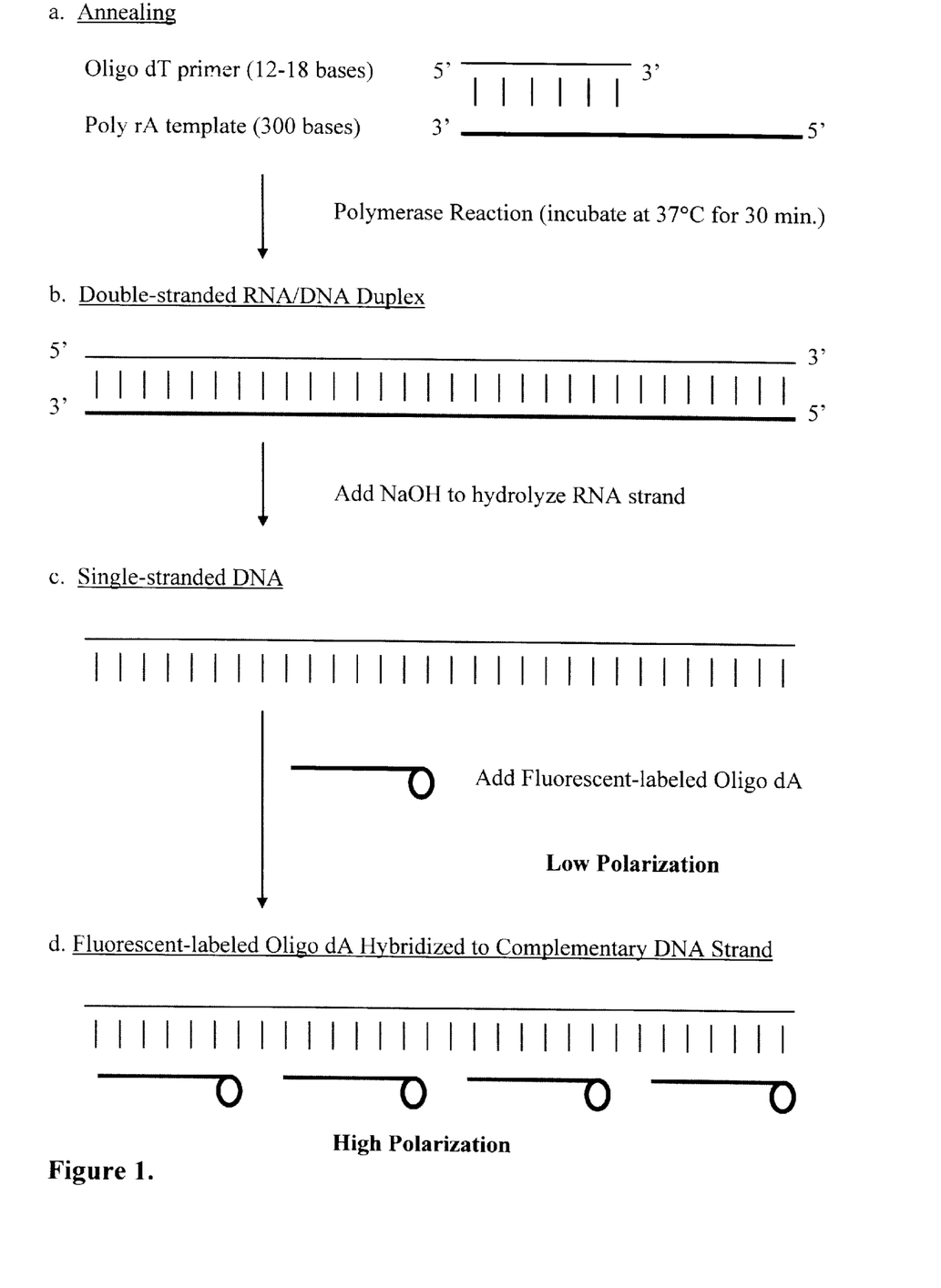
FIG. 1 shows a schematic of the fluorescence polarization reverse transcriptase process.

The general reaction scheme of the process is shown in FIG. 1. In step a. the Oligo dT primer (12–18 bases) is annealed to the Poly rA template. The reverse transcriptase reaction is allowed to incubate at 37° for 30 minutes. In step b. the RNA/DNA Duplex is hydrolyzed with NaOH. In step c. A fluorescent-labeled Oligo dA, with a low polarization value, is added to the resultant cDNA. In step d. the reaction is read on the Beacon 2000 Analyzer. A high polarization value results.

Example 2

Figure 2:
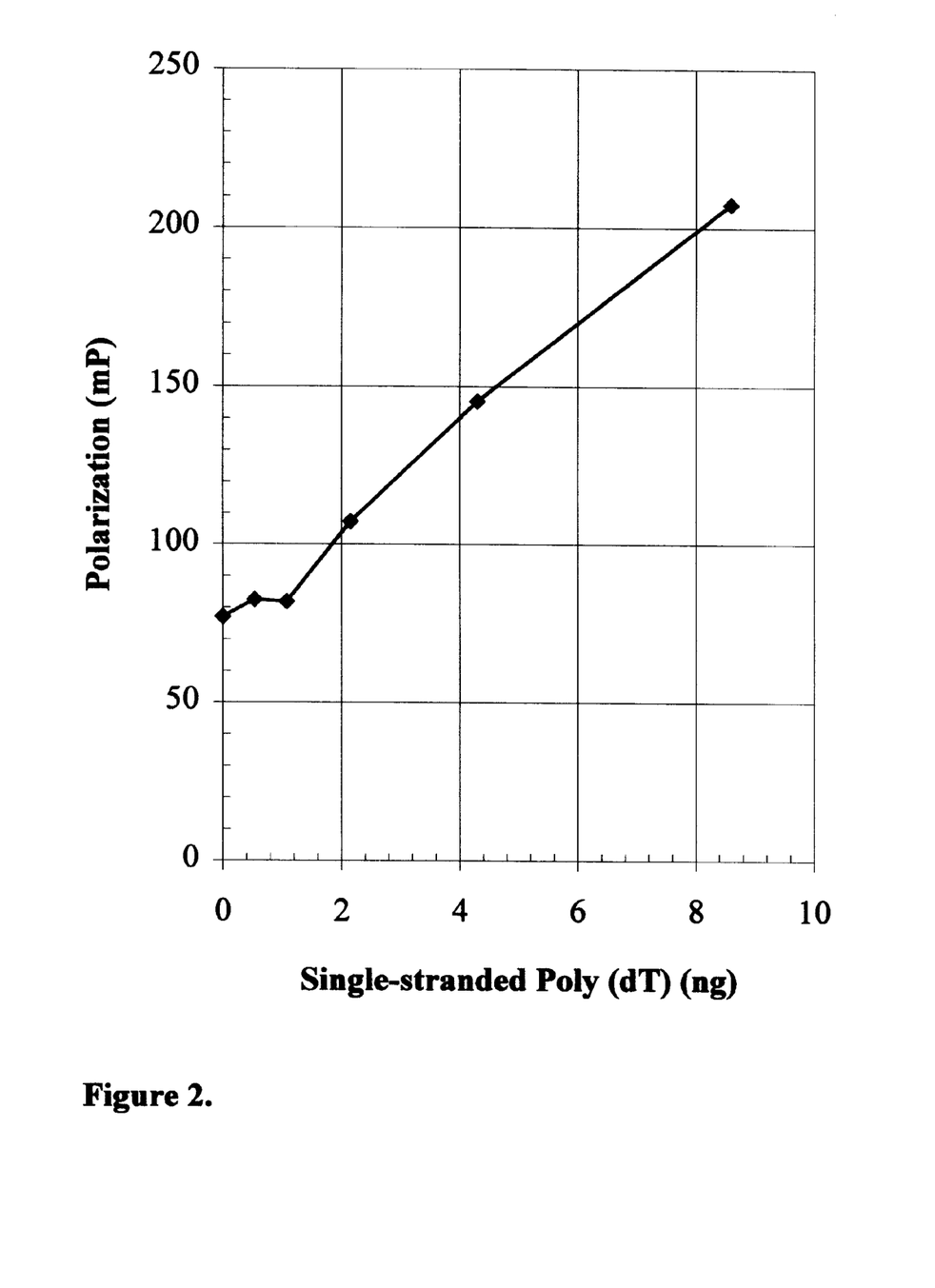
FIG. 2 illustrates detection of hybridization between serially diluted single-stranded poly (dT) and fluorescein-labeled oligo dA in single tube.

The shift in polarization of the Hybridized single-stranded Poly (dT)/DNA-Fluorescein-labeled Oligo dA (Oligo dA-F) complex is directly related to the concentration of Poly (dT) present, as shown in FIG. 2. The unbound Oligo dA-F has a low polarization value. When hybridized to a strand of Poly (dT) the polarization value increases. Poly (dT) was serially diluted from 8.6 ng to 500 pg in BGG Phosphate buffer to a final volume of 100 µl. Oligo dA-F was held constant and added to each dilution to a final concentration of 300 pM. The samples were allowed to incubate at room temperature for 10 minutes and polarization values were measured on the Beacon™ 2000 FP Analyzer. Excitation was measured at 485 nm and the emission measured at 535 nm. With increasing amounts of Poly (dT) the polarization value increases.

Example 3

Figure 3:
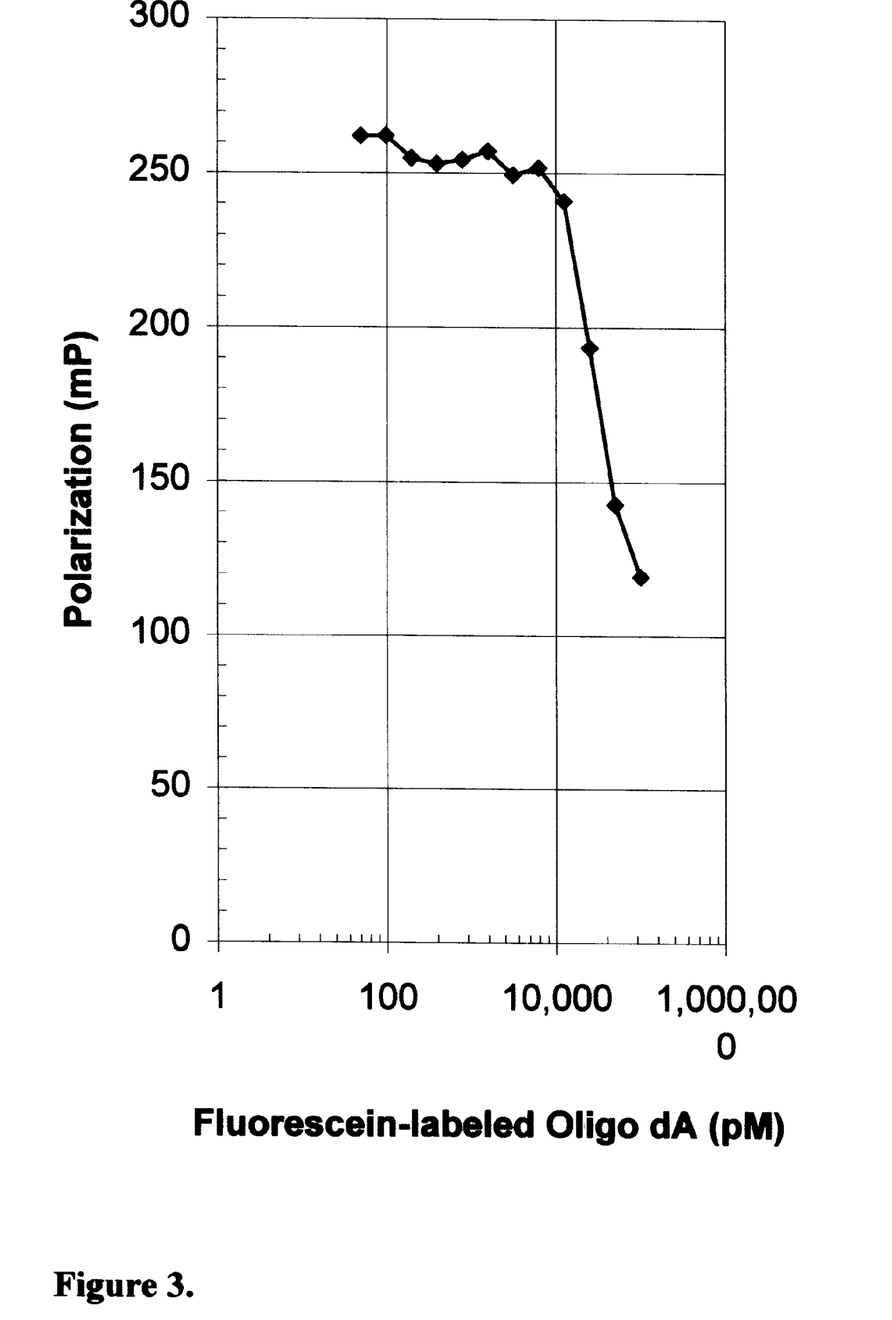
FIG. 3 illustrates detection of hybridization between serially diluted fluorescein-labeled oligo dA and single-stranded poly (dT) in single tube.

The experiment was performed as in Example 2 except that the single-stranded Poly (dT) was held constant and the Fluorescein-labeled Oligo dA was changed. Fluorescein-labeled Oligo dA was serially diluted from 100 NM to 49 pM in 0.5 M Tris-HCl, pH 7.5 to a final volume of 100 ul. Single-stranded Poly (dT) was added each dilution of Fluorescein-labeled Oligo dA to a final concentration of 160 pg/ul. The samples were allowed to incubate at room temperature for 10 minutes and polarization values measured on the Beacon™ 2000 FP Analyzer. FIG. 3 shows that as the Fluorescein-labeled Oligo dA concentration decreases the polarization value decreases.

Example 4

Figure 4:
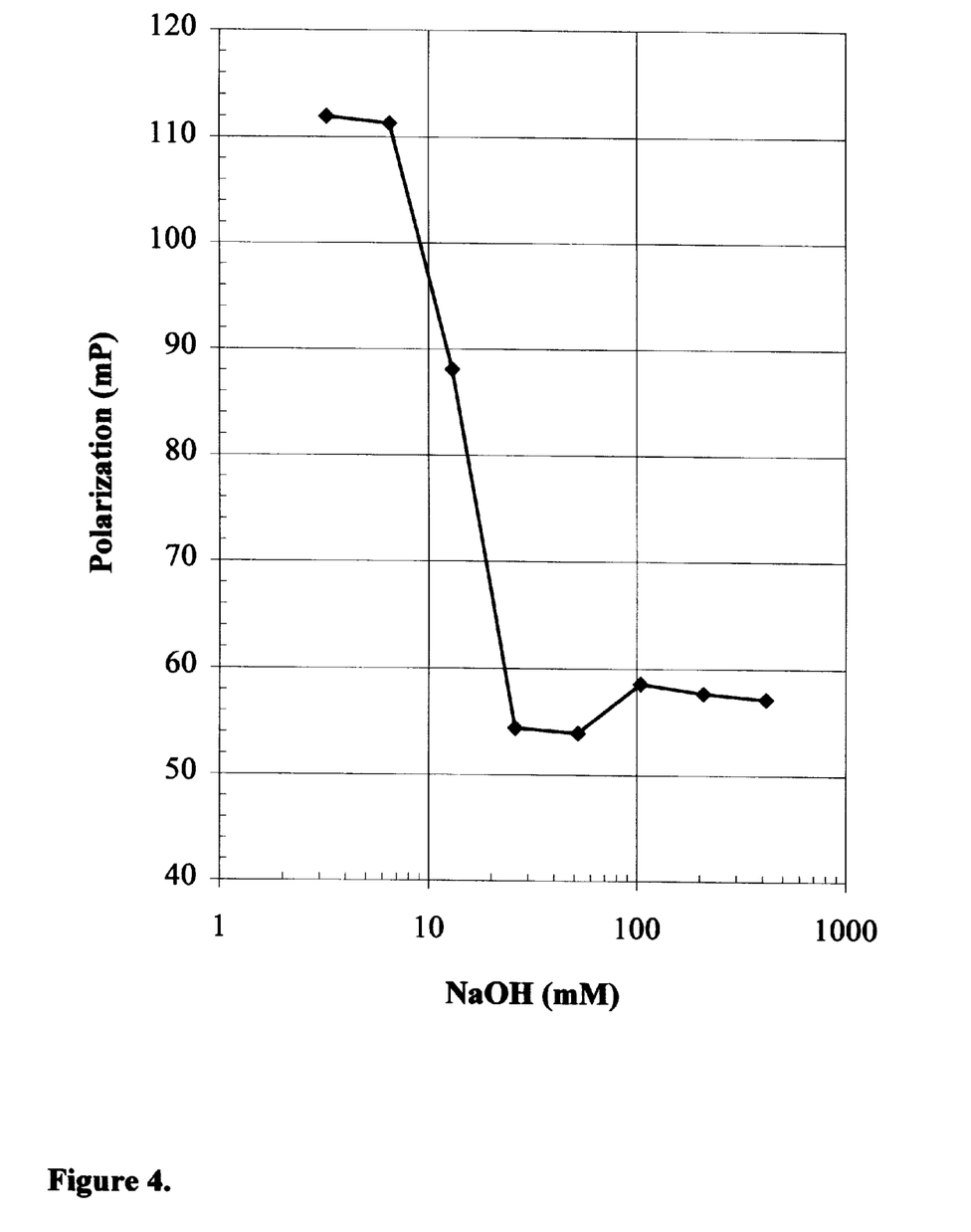
FIG. 4 illustrates detection of hydrolyzed fluorescein-labeled RNA.

Before the polymerase activity can be measured it is necessary to hydrolyze the RNA template. Following the polymerase reaction the RNA is hydrolyzed with sodium hydroxide. When a large RNA molecule is labeled with fluorescein it has a high starting polarization value. Therefore, sodium hydroxide is used to hydrolyze a Fluorescein-labeled RNA. To determine the minimum concentration necessary to hydrolyze the RNA strand, sodium hydroxide was serially diluted from 2.5M–20 mM. Twenty microliters of each dilution was added to 100 ul of 50 ug/ul Fluorescein-labeled RNA for a final volume of 120 ul. The final concentration of the sodium hydroxide ranged from 417 mM to 3.3 mM. The samples were measured immediately on the Beacon™ 2000 FP Analyzer. FIG. 4 shows the Fluorescein-labeled RNA being hydrolyzed (polarization value decreases as Fluorescein-labeled RNA is hydrolyzed).

Example 5

Figure 5:
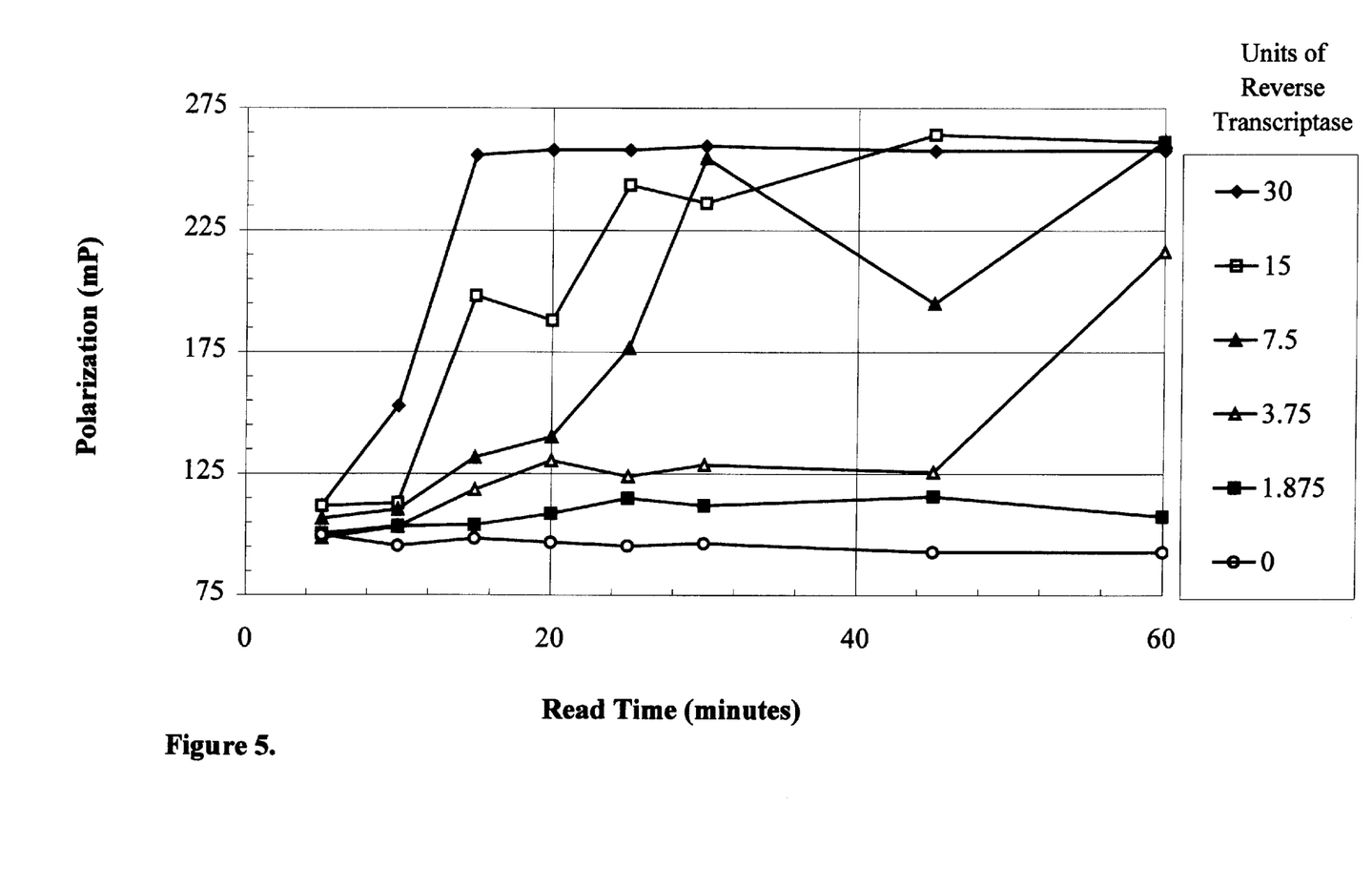
FIG. 5 illustrates a quantitative reverse transcriptase process using fluorescence polarization.

Reverse transcriptases play a key role in the propagation of retroviruses and are therefore key targets for the development of new therapeutics. The described process quantitatively measures the RNA-dependent DNA polymerase activity of reverse transcriptases using a homogeneous, non-radioactive fluorescent assay. An oligo-dT primer is hybridized to a 300 base poly-rA and extended with reverse transcriptase. The RNA/DNA duplex is treated with sodium hydroxide to hydrolyze the RNA strand, leaving the single-stranded DNA. Fluorescently labeled oligo-dA is then hybridized to the single-stranded DNA, causing a shift in polarization for the fluorescent oligonucleotide. When free, the fluorescent oligonucleotide has a low polarization value but when hybridized to the complementary DNA strand, it has a high polarization value. The shift in polarization is proportional to the amount of reverse transcriptase activity present. In the reaction, 20 ng of Oligo (dT) were annealed to 1 µg of Poly A at 70° C. for 5 minutes. The annealed reactions were added to an Reverse Transcriptase mix containing Reverse Transcriptase buffer and dTTP nucleotides with serially diluted reverse transcriptase (30, 15, 7.5, 3.8, and 1.9 Units/Rxn). Reactions were incubated at 37° C. in a water bath. 5 µl aliquots of each reaction were quenched at staggered time points of 5, 10, 15, 20, 25, 30, 45, and 60 minutes by adding the aliquots to a tube containing 20 µl of 125 mM NaOH. For the detection step, a 75 µl aliquot of fluorescein-labeled oligo dA in 0.5 M Tris, pH 7.5, was added to each quenched reaction. The samples were incubated for 10 minutes at room temperature. Fluorescence polarization in each sample was measured on the Beacon™ 2000 FP Analyzer. Increasing amounts of reverse transcriptase and subsequent time points produces shifts proportional to the amount of reverse transcriptase activity. No shift occurred in the absence of reverse transcriptase enzyme (see FIG. 5).

Example 6

Figure 6:
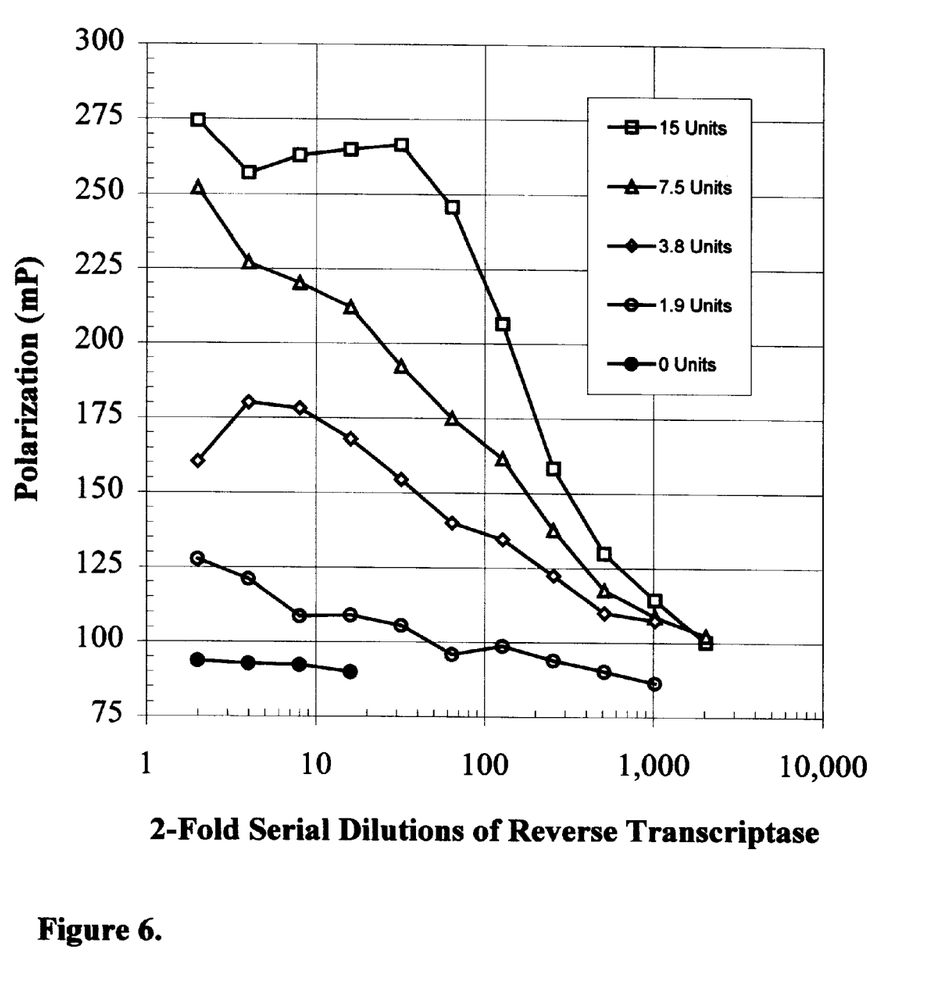
FIG. 6 illustrates the fluorescence polarization signal is proportional to the amount of reverse transcriptase present.

Reactions were set up as in Example 5 except reverse transcriptase was used at 0, 1.9, 3.8, 7.5, and 15 Units/Reaction and all reactions were quenched at 30 minutes. Each quenched reaction was then serially diluted from 1:2 to 1:2048 in 125 mM sodium hydroxide for a final volume of 25 ul. Then a 75 µl aliquot of fluorescein-labeled oligo dA in 0.5 M Tris, pH 7.5, was added to each quenched reaction. The samples were incubated for 10 minutes at room temperature and polarization measured on the Beacon™ 2000 FP Analyzer. The shift in polarization was proportional to increasing levels of reverse transcriptase added. No shift occurred in the absence of reverse transcriptase enzyme (see FIG. 6).

Example 7

Figure 7:
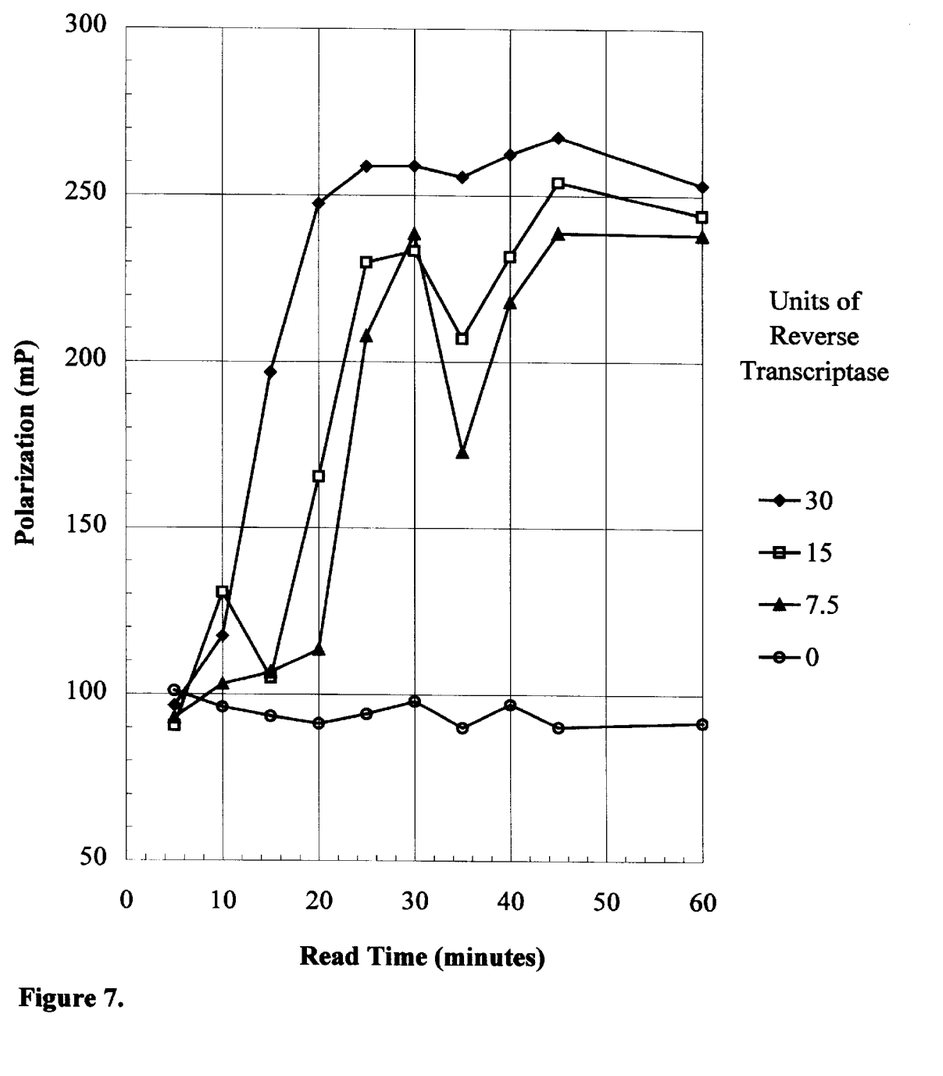
FIG. 7 illustrates the stability of the reverse transcriptase process using an immediate measurement.

Reactions were set up as in Example 5 except reverse transcriptase was used at 0, 7.5, 15, and 30 Units/Rxn. 5 ul aliquots of each reaction were quenched at staggered time points of 5, 10, 15, 20, 25, 30, 35, 40, 45, and 60 minutes by adding the aliquots to a tube containing 20 µl of 125 mM NaOH. For the detection step, a 75 µl aliquot of fluorescein-labeled oligo dA in 0.5 M Tris, pH 7.5, was added to each quenched reaction. Polarization was measured immediately then covered with parafilm and left at room temperature over night (see FIG. 7).

Example 8

Figure 8:
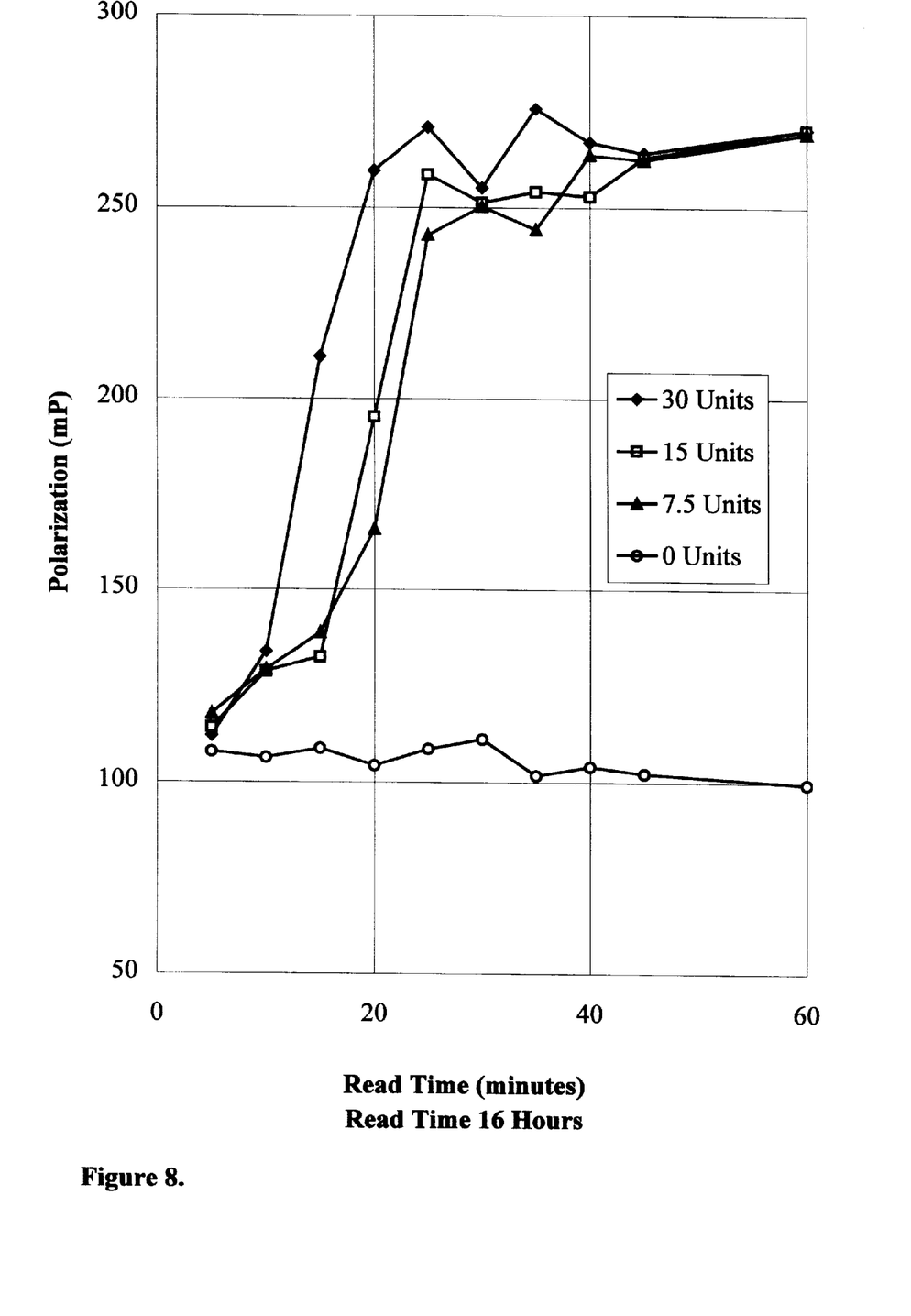
FIG. 8 illustrates the stability of the reverse transcriptase process using a 16 hour measurement.

The samples that were prepared in Example 7 were incubated at room temperature for 16 hours (overnight) and the polarization values were measured (necessary for high throughput screening applications, see FIG. 8).

The foregoing is considered as illustrative only of the principles of the invention. Further, since numerous modifications and changes will readily occur to those skilled in the art, it is not desired to limit the invention to the exact construction and operation shown and described. Therefore, all suitable modifications and equivalents fall within the scope of the invention.

We claim:

1. A process for detecting reverse transcriptase activity using fluorescence polarization, comprising:
   a) mixing a primer with an RNA template;
   b) forming an RNA/DNA duplex utilizing the reverse transcriptase;
   c) removing the RNA from the RNA/DNA duplex thereby forming a single-stranded DNA;
   d) adding a fluorescent-labeled oligonucleotide, having a known initial polarization value, for hybridizing to the single-stranded DNA;
   e) measuring a experimental fluorescence polarization; and,
   f) comparing the initial fluorescence polarization value with the experimental fluorescence value.

2. The process of claim 1 wherein the RNA template comprises a homopolymer for annealing anywhere along the length of the nucleic acid.

3. The process of claim 1 wherein removing the RNA comprises denaturation of the RNA.

4. The process of claim 1 wherein removing the RNA comprises base hydrolysis of the RNA.

5. The process of claim 2 wherein a plurality of the fluorescent-labeled oligonucleotide hybridizes to the single-stranded DNA for increased sensitivity.

6. The process of claim 2 wherein the homopolymer comprises polyriboadenlylic acid.

7. The process of claim 6 wherein the fluorescent-labeled oligonucleotide comprises polydeoxyriboadenylic acid.

8. The process of claim 7 wherein a plurality of the oligonucleotide polydeoxyriboadenylic acid hybridizes to the single-stranded DNA for increased sensitivity.

9. A process for quantifying formation of DNA from RNA by a reverse transcriptase, comprising:
   a) adding an RNA template to a solution to determine the activity of a reverse transcriptase and presence of reverse transcriptase inhibitors;
   b) forming an RNA/DNA duplex;
   c) forming a single-stranded DNA by removing the RNA from the RNA/DNA duplex;
   d) adding a light emitting labeled oligonucleotide having a known intitial polarization value, the oligonucleotide being complementary to the single-stranded DNA for hybridizing to the single-stranded DNA;
   e) detecting a experimental polarization value of the light emitting labeled oligonucleotide; and,
   f) comparing the initial polarization value with the experimental polarization value.

10. The process of claim 9 wherein the RNA template comprises a homopolymer for annealing anywhere along the length of the nucleic acid.

11. The process of claim 9 wherein removing the RNA comprises denaturation of the RNA.

12. The process of claim 9 wherein removing the RNA comprises base hydrolysis of the RNA.

13. The process of claim 9 wherein removing the RNA comprises adding an RNA removing enzyme.

14. The process of claim 9 wherein the light emitting labeled oligonucleotide comprises a fluorescent-labeled oligonucleotide.

15. The process of claim 10 wherein a plurality of the light-emitting labeled oligonucleotide hybridizes to the single-stranded DNA for increased sensitivity.

16. The process of claim 10 wherein the homopolymer comprises polyriboadenlylic acid.

17. The process of claim 16 wherein the light emitting labeled oligonucleotide comprises polydeoxyriboadenylic acid.

18. The process of claim 17 wherein a plurality of the oligonucleotide polydeoxyriboadenylic acid hybridizes to the single-stranded DNA for increased sensitivity.

19. A mixture for measuring reverse transcriptase activity, comprising:
   a) an RNA template;
   b) a plurality of DNA nucleotides complementary to the RNA template;
   c) an RNA removing enzyme for removing RNA from an RNA/DNA hybrid thereby forming single-stranded DNA; and,
   d) a light emitting labeled oligonucleotide complementary to the single-stranded DNA.

* * * * *